United States Patent
Shacknai et al.

(10) Patent No.: US 10,940,107 B2
(45) Date of Patent: Mar. 9, 2021

(54) FIBROBLAST MIXTURES AND METHODS OF MAKING AND USING THE SAME

(71) Applicant: DERMARCHÉ LABS, LLC, Scottsdale, AZ (US)

(72) Inventors: Jonah Shacknai, Scottsdale, AZ (US); Mitchell S. Wortzman, Scottsdale, AZ (US); David H. McDaniel, Virginia Beach, VA (US)

(73) Assignee: Dermaforce Holdings, LLC, Phoenix, AZ (US)

( * ) Notice: Subject to any disclaimer, the term of this patent is extended or adjusted under 35 U.S.C. 154(b) by 0 days.

(21) Appl. No.: 14/541,371

(22) Filed: Nov. 14, 2014

(65) Prior Publication Data
US 2015/0132267 A1    May 14, 2015

Related U.S. Application Data

(60) Provisional application No. 61/904,021, filed on Nov. 14, 2013.

(51) Int. Cl.
| | |
|---|---|
| *A61K 35/33* | (2015.01) |
| *A61K 8/98* | (2006.01) |
| *A61Q 19/08* | (2006.01) |
| *A61Q 19/00* | (2006.01) |
| *C12N 5/077* | (2010.01) |
| *A61K 9/00* | (2006.01) |

(52) U.S. Cl.
CPC ............ *A61K 8/981* (2013.01); *A61K 35/33* (2013.01); *A61Q 19/00* (2013.01); *A61Q 19/08* (2013.01); *C12N 5/0656* (2013.01); *A61K 9/0014* (2013.01); *A61K 2800/5922* (2013.01); *C12N 2502/1323* (2013.01)

(58) Field of Classification Search
None
See application file for complete search history.

(56) References Cited

U.S. PATENT DOCUMENTS

| | | | | |
|---|---|---|---|---|
| 7,118,746 B1 * | 10/2006 | Naughton | ................. | A23L 1/30 424/184.1 |
| 7,160,726 B2 * | 1/2007 | Mansbridge | ........... | A61K 8/447 424/198.1 |
| 2001/0048917 A1 | 12/2001 | Hoeffler et al. | | |
| 2007/0128174 A1 | 6/2007 | Kleinsek et al. | | |
| 2009/0016994 A1 * | 1/2009 | Gibbs | ................. | C12N 5/0698 424/93.7 |
| 2009/0239254 A1 * | 9/2009 | Duval | ................. | C12N 5/0698 435/29 |
| 2013/0095053 A1 * | 4/2013 | Hearing | ............. | A61K 38/1883 424/59 |
| 2013/0236427 A1 | 9/2013 | Pernock | | |

FOREIGN PATENT DOCUMENTS

| | | |
|---|---|---|
| CN | 102014866 A | 4/2011 |
| WO | 2009/121761 A1 | 10/2009 |
| WO | 2011/015862 A1 | 2/2011 |
| WO | 2013134248 A2 | 9/2013 |

OTHER PUBLICATIONS

Pinney et al., Wound healing potential of Dermagraft conditioned medium, Abstracts for the 61st Annual Meeting of the Society for Investigative Dermatology, May 10-14, 2000, Abstract 475, Journal of Investigative Dermatology, 114(4): 828 II, Accession: 036056222.*
Bernerd et al., Successive Alteration and Recovery of Epidermal Differentiation and Morphogenesis after Specific UVB-Damages in Skin Reconstructed in Vitro, Developmental Biology, vol. 183, pp. 123-138 (1997).*
Choi et al., The fibroblast-derived paracrine factor neuregulin-1 has a novel role in regulating the constitutive color and melanocyte function in human skin, Journal of Cell Science, vol. 123, pp. 3102-3111 (2010).*
Serum definition; retrieved from the internet: www.Dictionary.com.*
MerriamWebster definitions: Human Race, Ethnic and Ethnicity: retrieved from the internet at www.merriam-webster.com.*
Ehrlich et al., Dermatologic Surgery, 32:5: May 2006, pp. 618-625 (Year: 2006).*
Fantasia et al., Journal of Dermatological Science, vol. 70, 2013, pp. 159-165 (Year: 2013).*
Okazaki et al., Journal of Dermatological Science, vol. 30 (2002), pp. 108-115 (Year: 2002).*
Burke et al. Dermatologic Therapy, vol. 20 2007, pp. 314-321 (Year: 2007).*
International Search Report dated Jan. 29, 2015 from corresponding International Patent Application No. PCT/US2014/065627, 3 pages.
Written Opinion dated Jan. 29, 2015 from corresponding International Patent Application No. PCT/US2014/065627, 9 pages.
Inernational Preliminary Report on Patentability dated May 17, 2016 from corresponding International Application No. PCT/US2014/065627, 7 pages.
Extended European Search Report dated Apr. 11, 2017 from corresponding European Patent Application No. 14861312.8, 16 pages.
Chinese First Office Action dated Feb. 3, 2019 from corresponding Chinese Patent Application No. 201480062569.9, 14 pages.

(Continued)

*Primary Examiner* — Scott Long
*Assistant Examiner* — Evelyn Y Pyla
(74) *Attorney, Agent, or Firm* — Ohlandt, Greeley, Ruggiero & Perle, L.L.P.

(57) ABSTRACT

The present disclosure provides a non-autologous product that is a mixture of two or more cells or tissue cultures of fibroblast, or extracts from cultures, or media cultures, isolated from separate individuals, either homogeneous or heterogeneous. The cells or factors are blended together in a product that imparts desired characteristics to the skin of a recipient who is not a source of the mixture. The present disclosure also relates to methods of making and using and/or culturing the fibroblasts including to optimize the potency of the mixture to impart one or more the desired characteristics to the skin of a recipient.

11 Claims, 2 Drawing Sheets

(56) References Cited

OTHER PUBLICATIONS

Vincent J. Cristofalo, Robert G. Allen, Robert J. Pignolo, Bernard G. Martin, Jeanne C. Beck Relationship between donor age and the replicative lifespan of human cells in culture: A reevaluation; Proceedings of the National Academy of Sciences Sep. 1998, 95 (18) 10614-10619.

K Bayreuther, H P Rodemann, R Hommel, K Dittmann, Malbiez, P I Francz, Human skin fibroblasts in vitro differentiate along a terminal cell lineage, Proceedings of the National Academy of Sciences Jul. 1988, 85 (14) 5112-5116.

Saed, Ghassan M et al. Hypoxia-induced irreversible up-regulation of type I collagen and transforming growth factor-β1 in human peritoneal fibroblasts, Fertility and Sterility, vol. 78, Issue 1, 144-147.

Chinese Office Action dated Sep. 20, 19 in corresponding Chinese Patent Application No. 201480062569.9, 7 pages.

Japanese Office Action dated Sep. 3, 2019 in corresponding Japanese Divisional Patent Application No. 2018-177515, 8 pages.

Japanese Office Action for corresponding application JP2016-554319, 8 pages, dated Aug. 1, 2017.

\* cited by examiner

US 10,940,107 B2

FIBROBLAST MIXTURES AND METHODS OF MAKING AND USING THE SAME

RELATED APPLICATION

This application claim priority in U.S. provisional application Ser. No. 61/904,021, filed Nov. 14, 2013, which is incorporated herein by reference.

BACKGROUND OF THE DISCLOSURE

1. Field of the Disclosure

The present disclosure relates to a mixture of two or more tissue cultures of fibroblast, or extracts from cultures, or media cultures isolated from separate individuals, either homogeneous or heterogeneous. The present disclosure further relates to the use of such fibroblast cultures, coculture of cells, extracts from cells, diffusible elements that form the cell culture or culture media, either alone or with environmental conditions, to grow the cells and induce them to produce their array of factors or elements produced by or extracted from the cells. The present disclosure still further relates that these cells or factors are blended together in a product that imparts desired characteristics to the skin of a recipient who is not a source of the mixture and any individual fibroblasts, namely non-autologous. The present disclosure also relates to methods of making and using and/or culturing the fibroblasts and the mixtures thereof including methods for optimizing the potency or potential of the cells or factors in a mixture to impart the desired characteristics to the recipient's skin.

2. Description of the Related Art

One of the primary functions of a fibroblast is to maintain the structural integrity of connective tissues by continuously secreting precursors of the extracellular matrix. A fibroblast secretes precursors of all components of the extracellular matrix, primarily the ground substance and a variety of fibers or structural proteins. They also secrete small molecular weight diffusible factors that influence and coordinate the function and product of neighboring cells to enhance tissue response. The composition of the extracellular matrix significantly determines the physical properties of connective tissues.

Known in the art are methods of treatment using autologous fibroblasts (i.e. fibroblast obtained from a donor who will also be the recipient of cultured fibroblasts). Among the known uses of such fibroblasts are a method of promoting healing of wounds, such as an epithelial wound or fistula, by administering cultured fibroblasts; a method of corrective surgery by the augmentation of tissue sub-adjacent to a vocal cord defect; and a method of treatment of vocal fold scarring and repair of skin and soft tissue defects.

Also known in the art are dosage units consisting of autologous fibroblasts grown for an individual who is also the donor. Further, there are known methods of growing fibroblasts for use in autologous applications.

Deriving a commercial, non-autologous product from a mixture of two or more tissue cultures of fibroblast or extracts from cultures or media cultures isolated from separate individuals, either homogeneous or heterogeneous

SUMMARY OF THE DISCLOSURE

The present disclosure provides a non-autologous product.

The present disclosure further provides such a non-autologous product that is a homogeneous and heterogeneous mixture of two or more fibroblasts cultures, extracts derived therefrom, and/or diffusible elements recovered from the culture media from the same sex.

The present disclosure also provides that each mixture of homogeneous and/or heterogeneous fibroblasts cultures or extracts therefrom from the same sex can have "weighted" factors based on the characteristics desired to be obtained by the mixture.

The present disclosure still further provides that the fibroblast cultures or extracts therefrom or the diffusible elements that form the cell culture can be influenced to produce variations in the product or resultant product.

The present disclosure, in addition, provides that for each product there can be at least three factors with one or more factors having greater weight.

The present disclosure yet provides that the factors include, but are not limited to, age, DNA testing, ethnic homogeneity, health, physical beauty (adherence to classic beauty as described by the golden ratio, sometimes referred to as a Fibronacci series) to produce or create variations in the product or different resultant products. These different resultant products can be directed to enhance, modulate or treat one or more desired characteristics of the user of the composition of the present disclosure.

The present disclosure further provides methods of using the heterogeneous and/or homogeneous mixtures of fibroblasts or extracts therefrom or the diffusible elements that form the cell culture, from the same sex, to provide a non-autologous product.

The present disclosure additionally provides methods of making, i.e. culturing, of the mixture including aspects of enhancing the beneficial effects or modulating the effects of the mixture.

DESCRIPTION OF THE PREFERRED EMBODIMENTS

Figure 1:
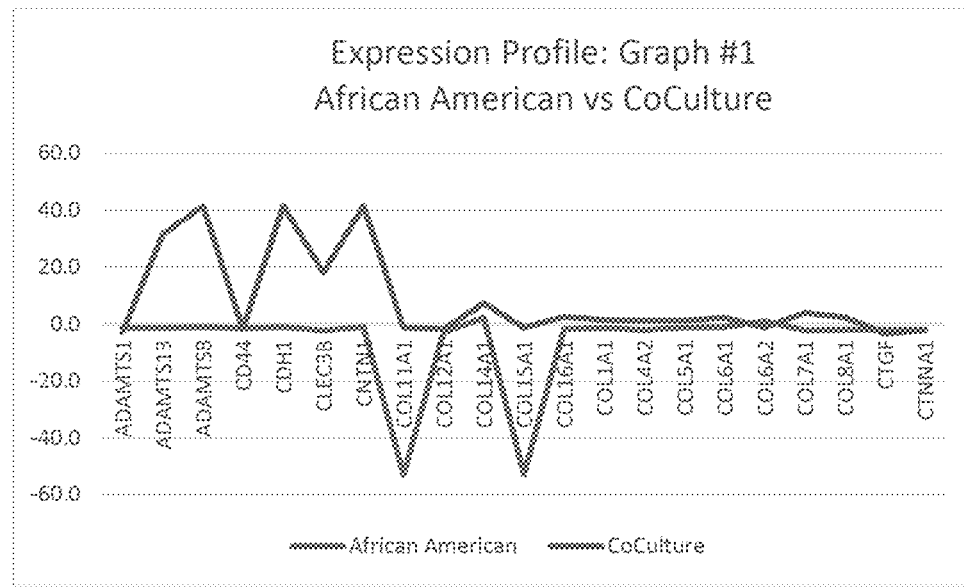
FIGS. 1 to 4 are graphs of test results that demonstrate differences in the overall expression profiles.

As stated above, the present disclosure provides a mixture of two or more tissue cultures of fibroblasts, coculture of cells, extracts from cells or cultures, diffusible elements that form the cell culture, or culture media isolated from separate individuals, whether homogeneous and heterogeneous from the same sex. The use of fibroblast cultures, coculture of cells, extracts from cells or cultures, diffusible elements that form the cell culture, or culture media, either alone or with environmental conditions, are used to grow cells and induce the cells to produce their array of elements produced by or extracted from the cells. These cells, cultures, coculture of cells, diffusible elements that form the cell culture and culture media and/or factors are blended together in a product that imparts desired characteristics to the skin of a recipient. Significantly, since the recipient is not the source of the mixture or any individual fibroblast, the relationship between the recipient and the fibroblasts is referred to as "non-autologous". Since the products are intended for a specific sex, namely women or men, the blend of cells, cocultures, cultures, diffusible elements that form the cell culture, and culture media and/or elements in each product are derived from the desired sex.

These elements produced by or extractable from the cells, cultures, culture media and/or elements as stated above, are blended together and included in the product. The elements include, but are not limited to, growth factors including epidermal growth factors, proteins, peptides, cytokines and all other biomolecules present in the cell or media culture.

According to the present disclosure, the product will preferably be a topical composition. The preferred topical composition is a cream, serum or lotion. The composition can include delivery vehicles, such as liposomes and micelles. The composition can also include transport molecules, such as a protein or a macromolecule that promotes or provides molecular sledding. The use of such transport molecules enables delivery of the elements to the epidermis or dermis of a recipient. However, the composition can be parental (e.g. injectable, intravenous, or the like), delivered by device (e.g. laser, micronneedle, inhaler, or the like), or an oral periodontal including a mouthwash.

The tissue culture fibroblasts or fibroblast cells or cultures or extracts from cultures, diffusible elements that form the cell culture, or media cultures can also be influenced to produce variations in the array of elements produced by or extractable from the cells or media culture, the amount and type of elements, due to the exposure to different chemical, culture or environmental elements of the growth medium of the cultures. For example, oxygen level (hypoxia, hyperoxia, and normative oxygen levels), AOX, pH, temperature, and exposure of the cells to different levels of UV light and different mixtures of UVA, UVB, UVC, IR, and visible light, can effect or influence the fibroblast cultures or extracts therefrom. Further, environmental conditions can affect the culture fibroblasts, or fibroblast cultures, or extracts from cultures, or media cultures, or elements. Such environmental conditions include, but are not limited to, PO2, CO, (hyper or hypo oxygen conditions) exposure to different bands of UV or other forms of energy, temperature and the like.

As used herein, the term "homogeneous" means the use of fibroblast cultures obtained from donors who constitute a group whose bloodlines are 80% or greater of a single race or ethnicity, preferably 90% or greater, more preferably 95% or greater, and most preferably essentially 100%. Thus, a fibroblast culture obtained from a homogeneous set of donors (of the same-sex), such as a group of: Japanese women, or West African women, or Indian women. Because of centuries-old racial intermixes, the term "homogeneous" generally does not apply to groups selected from cultures such as, for example, those in America or the Caribbean Islands.

The term "heterogeneous", as used herein, means the use of non-ethnic homogeneity fibroblasts, such as fibroblasts obtained from same-sex, but a combination of different groups or sources, such as, for example, a group of: West African women and Japanese women, or West African women and Indian women, or Japanese women and Western European women.

The mixtures of homogeneous and/or heterogeneous tissue cultures of fibroblasts of the present disclosure can be "tailored" to include more of one ethnic group than another. Further, the "tailoring" can include consideration of factors that are "weighted" based on the characteristics desired to be obtained by the mixture. The factors include, but are not limited to, age, DNA testing, ethnic homogeneity, health, and physical beauty (adherence to classic beauty as described by the golden ratio, sometimes referred to as a Fibronacci series), to produce variations in the product or different resultant products. These different resultant products can be directed to enhance one or more desired characteristics of the user of the composition of the present disclosure.

For example, a mixture of tissue cultures of fibroblasts can comprise 50% fibroblasts from a West African woman, 30% fibroblasts from a Japanese woman, and 20% fibroblasts from an Indian woman. Each percentage can be obtained from either a single woman or a group of women constituting a homogenous mixture, as the term homogenous has been defined above, such as a plurality of women from the West African nation of Mali. The selection of the fibroblasts and the weighing of factors for the mixture are predicated on the particular pigment or other characteristic desired to be improved or imparted to the skin of a recipient. Thus, it should be understood that according to one embodiment of the present disclosure, the composition provides a selection of ethnic group or groups of donors and possibly a "weighted" mixture to achieve a resultant product that delivers at least one property, preferably to the skin. The one property can be, for example, enhanced skin firmness or smoothness, or more fullness of the skin. Moreover, that one property can be improved on virtually any person (of any ethnic background) that uses the composition of this embodiment of the present disclosure.

The particular characteristics desired to be imparted to the skin of a recipient can include, but are not limited to, skin tone, skin elasticity, skin smoothness, reduced scarring, reduced wrinkles, response to inflammatory stimulus, ability to retain moisture, propensity to produce new vasculature and deliver nutrients and skin thickness or density, improve response to injury or free-radical damage, or combination of skin characteristics that will be apparent to those of skill in the art based upon the present disclosure. Because the mixtures of homogeneous and/or heterogeneous fibroblast cultures can be "tailored" to provide a specific desirable skin characteristic or combination of skin characteristics, the present disclosure provides limitless possibilities for imparting characteristics to the skin of a recipient. Thus, "tailoring" can include a larger percentage of fibroblast cultures from one homogeneous or heterogeneous woman of group of women since that woman or group are known or believed to provide the desired characteristic.

It is believed that skin wrinkling is a problem of lighter skin types. Also, mottled hyperpigmentation and uneven skin tone is associated with the darker skin types. Further, Asian descents have mechanisms to protect against photoaging. Thus, the above can be considered in deciding the tailoring including weighing based on the skin characteristic or combination of skin characteristics desired in the product. As shown by the test data below, increased HAS1 in CoCulture relative to one group (or monoculture) shows both improved antiwrinkling and photodamage prevention or minimalization. This underscores the ability to produce compositions according to the present disclosure in which tailoring or customization of a composition is achievable. The test data in the present disclosure proves that any combination of cells or cocultures, and supports the belief that any combination of extracts from cells or cultures, diffusible elements that form the cell culture, culture media or external factors, can add Col1a1 stimulation and/or MMP1 suppression to HAS1 (hyaluronic acid) production in a composition to produce an anti-aging product.

In a preferred embodiment, it is believed that the "weighed" mixture, has a hierarchy among the factors. Preferably, for an ethnic homogeneity, (1) health, (2) age, and (3) beauty factors in this order of priority are considered.

Concerning the health factor, it is important to consider eliminating donors having a genetic disease. Also, premature aging due to environmental conditions, such as free radical generating, namely sun and higher neoplasms, as well as premature aging due to smoking, should be eliminated from the donor "pool".

For the age factor, the donor "pool", especially of women, the age of the donors from which the fibroblasts are derived is preferably of a young age since their skin and fibroblasts are at an optimal state of life. Such an age range can vary based on ethnicity. It is believe that the preferred age range is from 18 to 35, more preferably 18 to 30 years of age. However, it is envisioned that the age range can have a lower limited possibly to the age of a mature individual, which in the U.S. is a teenager, namely about 12 years of age.

For the beauty factor, the adherence to classic beauty as described by the golden ratio, sometimes referred to as a Fibronacci series, has a number of desirable features. These desirable features include, but are not limited to, the geometric relationship between the angles and spacings of key features or elements of the face including, but not limited to, the mouth, eyes, and arch of brow. The selection of such features will be included in the "tailoring" of the eventual product. Thus, products can be made to be customized to the intended recipients.

As discussed above, it is also believed that the present disclosure can be used for other purposes. For example, the present compositions can be used to heal a wound or to mitigate scarring. Thus, it is envisioned that the intra epidermal, dermal and SQ, not just the epidermis layer, can be affected by the compositions and methods of the present disclosure.

The present disclosure also provides methods of making, i.e. culturing, fibroblast mixtures and, moreover, optimizing such culturing. As well known, the fibroblast cultures can take a significant amount of time to grow to sufficient numbers and generally require multiple passages of the fibroblasts in culture media to obtain satisfactory yields. Also, the method of making the fibroblasts can be modified by processes, such as, external and/or environmental elicitation. Further, the fibroblasts can be genetically modified. Still further, the fibroblasts can be converted from the skin or non-skin sources, such as, for example, umbilical cord mesenchymal stem cells. According to the present disclosure, the fibroblast cultures can be obtained from an animal, such as a mammal, in accordance with methods known in the art. Preferably, the fibroblast cultures are obtained by isolating fibroblasts from the same type of tissue that is the object of the methods of use of the present disclosure. Methods of culturing fibroblasts including culture media and culturing techniques, such as passaging and selection are also known in the art. Usual cultured media include bovine serum albumin or fetal calf serum that is FBS free. However, the fibroblasts can be cultured in serum mixture of the donors. Preferably, collagen-producing fibroblasts are selected.

The present disclosure envisions that the potencies of the fibroblast culture mixture obtained according to the methods of making can be beneficially modified for improved efficacy or optimization. For example, improved potency or altering elements can be achieved by modifying the oxygen level under which the culturing and fibroblast growth is performed. It is possible to modulate the potency of the homogeneous and/or heterogeneous fibroblast culture mixture by adjusting the oxygen level under which the fibroblasts are cultured.

In combination with the ability to prepare the "tailored" "weighted" mixtures of homogeneous and/or heterogeneous fibroblast cultures, the ability to modulate the potency of the resulting fibroblast cultured mixture by adjusting the option level under which the mixtures of fibroblast cultures are grown provides a wide range of options, including therapeutic options, according to the present disclosure.

As discussed herein, in a preferred embodiment directed to women. However, the present disclosure can also be used for men. Thus, there can the same principals and teachings applied, as discussed above, for men.

Human skin fibroblasts from female humans of African American [African America group] and Asian [Asian/Korean group] background of a low passage were seeded into 6 well dishes. This was done for both groups in single culture and in a 50:50 combination ratio of African American to Asian/Korean. The cells were cultured until approximately twenty-four (24) hours after the cells reached confluency (tightly packed monolayer). At 24 hours post confluency, cells were then lysed and RNA extracted using a phenol:chloroform extraction method (Trizol Reagent). The RNA was then quantified and concentration of RNA evaluated. This RNA was converted to cDNA using the SABiosciences $RT^2$ Easy First Strand kit. The cDNA was mixed with SYBR green detection agent and added to the wells of other SABiosciences $RT^2$ ECM and Adhesion molecule array, per kit instructions. The array was loaded into a Bio-Rad iCycler for array performance and data capture. Analysis was performed using web based software designed specifically for the array.

The results of one experimental replicates per parameter were evaluated from the web based software for fold regulation changes between control and exposed cells, and statistical significance/p-value determination. The genes on the array(s) were then examined for dysregulation (with or without statistical significance) to determine what areas of the array have the most dysregulation and are most likely to be the processes effected. Since only one array per sample was run, p-values could not be generated and values listed below were only be analyzed for biological significance (greater than 2 fold increase or decreased gene expression value relative to control). All gene values were normalized to HPRT1,B2M, GAPDH and RPLP0 in the Control Gene List. The Asian/Korean group of cells were set as the Control sample, so the following comparisons are gene dysregulation relative to Asian/Korean expression levels as set forth in the Gene Expression Value Summary Table below.

| Symbol | Description | African American Fold Change | 1:1 Ratio Asian:African American Fold Change |
|---|---|---|---|
| ADAMTS1 | ADAM metallopeptidase with thrombospondin type 1 motif, 1 | −1.3 | −2.7 |
| ADAMTS13 | ADAM metallopeptidase with thrombospondin type 1 motif, 13 | −1.3 | 31.5 |
| ADAMTS8 | ADAM metallopeptidase with thrombospondin type 1 motif, 8 | −1.0 | 41.5 |

-continued

| Symbol | Description | African American Fold Change | 1:1 Ratio Asian:African American Fold Change |
|---|---|---|---|
| CD44 | CD44 molecule (Indian blood group) | −1.4 | −1.7 |
| CDH1 | Cadherin 1, type 1, E-cadherin (epithelial) | −1.0 | 41.5 |
| CLEC3B | C-type lectin domain family 3, member B | −2.2 | 18.1 |
| CNTN1 | Contactin 1 | −1.0 | 41.5 |
| COL11A1 | Collagen, type XI, alpha 1 | −52.9 | −1.3 |
| COL12A1 | Collagen, type XII, alpha 1 | −2.9 | −1.8 |
| COL14A1 | Collagen, type XIV, alpha 1 | 2.3 | 7.3 |
| COL15A1 | Collagen, type XV, alpha 1 | −52.9 | −1.3 |
| COL16A1 | Collagen, type XVI, alpha 1 | −1.8 | 2.6 |
| COL1A1 | Collagen, type I, alpha 1 | −1.4 | 1.5 |
| COL4A2 | Collagen, type IV, alpha 2 | −2.0 | 1.1 |
| COL5A1 | Collagen, type V, alpha 1 | −1.2 | 1.2 |
| COL6A1 | Collagen, type VI, alpha 1 | −1.0 | 2.3 |
| COL6A2 | Collagen, type VI, alpha 2 | 1.1 | −1.1 |
| COL7A1 | Collagen, type VII, alpha 1 | −2.2 | 3.9 |
| COL8A1 | Collagen, type VIII, alpha 1 | −1.9 | 2.4 |
| CTGF | Connective tissue growth factor | −1.9 | −3.3 |
| CTNNA1 | Catenin (cadherin-associated protein), alpha 1, 102 kDa | −2.0 | −2.0 |
| CTNNB1 | Catenin (cadherin-associated protein), beta 1, 88 kDa | −1.0 | 41.5 |
| CTNND1 | Catenin (cadherin-associated protein), delta 1 | −1.3 | 5.6 |
| CTNND2 | Catenin (cadherin-associated protein), delta 2 (neural plakophilin-related arm-repeat protein) | −1.0 | 41.5 |
| ECM1 | Extracellular matrix protein 1 | −1.3 | −1.3 |
| FN1 | Fibronectin 1 | −1.4 | −1.5 |
| HAS1 | Hyaluronan synthase 1 | −1.0 | 41.5 |
| ICAM1 | Intercellular adhesion molecule 1 | 2.3 | 11.9 |
| ITGA1 | Integrin, alpha 1 | −5.0 | −3.3 |
| ITGA2 | Integrin, alpha 2 (CD49B, alpha 2 subunit of VLA-2 receptor) | −3.1 | −2.7 |
| ITGA3 | Integrin, alpha 3 (antigen CD49C, alpha 3 subunit of VLA-3 receptor) | −2.3 | −1.2 |
| ITGA4 | Integrin, alpha 4 (antigen CD49D, alpha 4 subunit of VLA-4 receptor) | −2.0 | −4.7 |
| ITGA5 | Integrin, alpha 5 (fibronectin receptor, alpha polypeptide) | −1.8 | 1.2 |
| ITGA6 | Integrin, alpha 6 | −2.5 | −1.4 |
| ITGA7 | Integrin, alpha 7 | −2.2 | 10.4 |
| ITGA8 | Integrin, alpha 8 | −2.0 | 3.2 |
| ITGAL | Integrin, alpha L (antigen CD11A (p180), lymphocyte function-associated antigen 1; alpha polypeptide) | 2.0 | 41.5 |
| ITGAM | Integrin, alpha M (complement component 3 receptor 3 subunit) | 1.5 | 41.5 |
| ITGAV | Integrin, alpha V (vitronectin receptor, alpha polypeptide, antigen CD51) | −1.2 | −2.0 |
| ITGB1 | Integrin, beta 1 (fibronectin receptor, beta polypeptide, antigen CD29 includes MDF2, MSK12) | −1.8 | −11.5 |
| ITGB2 | Integrin, beta 2 (complement component 3 receptor 3 and 4 subunit) | −1.3 | 31.5 |
| ITGB3 | Integrin, beta 3 (platelet glycoprotein IIIa, antigen CD61) | 1.1 | 6.8 |
| ITGB4 | Integrin, beta 4 | −1.0 | 41.5 |
| ITGB5 | Integrin, beta 5 | −3.1 | −2.3 |
| KAL1 | Kallmann syndrome 1 sequence | −1.0 | 41.5 |
| LAMA1 | Laminin, alpha 1 | −1.0 | 41.5 |
| LAMA2 | Laminin, alpha 2 | −3.3 | −1.7 |
| LAMA3 | Laminin, alpha 3 | −7.6 | 5.6 |
| LAMB1 | Laminin, beta 1 | −1.3 | −1.5 |
| LAMB3 | Laminin, beta 3 | 27.4 | 54.8 |
| LAMC1 | Laminin, gamma 1 (formerly LAMB2) | −1.5 | −2.0 |
| MMP1 | Matrix metallopeptidase 1 (interstitial collagenase) | −16.3 | −13.2 |
| MMP10 | Matrix metallopeptidase 10 (stromelysin 2) | −1.0 | 41.5 |
| MMP11 | Matrix metallopeptidase 11 (stromelysin 3) | −1.3 | 19.4 |
| MMP12 | Matrix metallopeptidase 12 (macrophage elastase) | −1.3 | 31.5 |
| MMP13 | Matrix metallopeptidase 13 (collagenase 3) | −1.0 | 41.5 |
| MMP14 | Matrix metallopeptidase 14 (membrane-inserted) | −1.9 | −1.9 |

| Symbol | Description | African American Fold Change | 1:1 Ratio Asian:African American Fold Change |
|---|---|---|---|
| MMP15 | Matrix metallopeptidase 15 (membrane-inserted) | 8.4 | 41.5 |
| MMP16 | Matrix metallopeptidase 16 (membrane-inserted) | −4.1 | −2.7 |
| MMP2 | Matrix metallopeptidase 2 (gelatinase A, 72 kDa gelatinase, 72 kDa type IV collagenase) | −2.5 | −1.4 |
| MMP3 | Matrix metallopeptidase 3 (stromelysin 1, progelatinase) | −10.7 | −5.4 |
| MMP7 | Matrix metallopeptidase 7 (matrilysin, uterine) | −1.0 | 41.5 |
| MMP8 | Matrix metallopeptidase 8 (neutrophil collagenase) | −1.0 | 41.5 |
| MMP9 | Matrix metallopeptidase 9 (gelatinase B, 92 kDa gelatinase, 92 kDa type IV collagenase) | −1.0 | 41.5 |
| NCAM1 | Neural cell adhesion molecule 1 | −1.9 | 9.0 |
| PECAM1 | Platelet/endothelial cell adhesion molecule | 2.8 | 18.1 |
| SELE | Selectin E | −1.0 | 41.5 |
| SELL | Selectin L | −1.0 | 41.5 |
| SELP | Selectin P (granule membrane protein 140 kDa, antigen CD62) | −1.0 | 41.5 |
| SGCE | Sarcoglycan, epsilon | 1.1 | 1.8 |
| SPARC | Secreted protein, acidic, cysteine-rich (osteonectin) | −3.5 | −1.7 |
| SPG7 | Spastic paraplegia 7 (pure and complicated autosomal recessive) | −1.5 | 1.7 |
| SPP1 | Secreted phosphoprotein 1 | −5.8 | 3.9 |
| TGFBI | Transforming growth factor, beta-induced, 68 kDa | −2.7 | −3.8 |
| THBS1 | Thrombospondin 1 | −1.7 | −17.4 |
| THBS2 | Thrombospondin 2 | −2.3 | −1.2 |
| THBS3 | Thrombospondin 3 | −1.0 | 41.5 |
| TIMP1 | TIMP metallopeptidase inhibitor 1 | −1.8 | −1.3 |
| TIMP2 | TIMP metallopeptidase inhibitor 2 | −1.5 | −1.3 |
| TIMP3 | TIMP metallopeptidase inhibitor 3 | −6.2 | −8.7 |
| TNC | Tenascin C | −1.3 | 1.1 |
| VCAM1 | Vascular cell adhesion molecule 1 | −1.0 | 41.5 |
| VCAN | Versican | −3.3 | −10.0 |
| VTN | Vitronectin | −1.0 | 41.5 |

Figure 2:
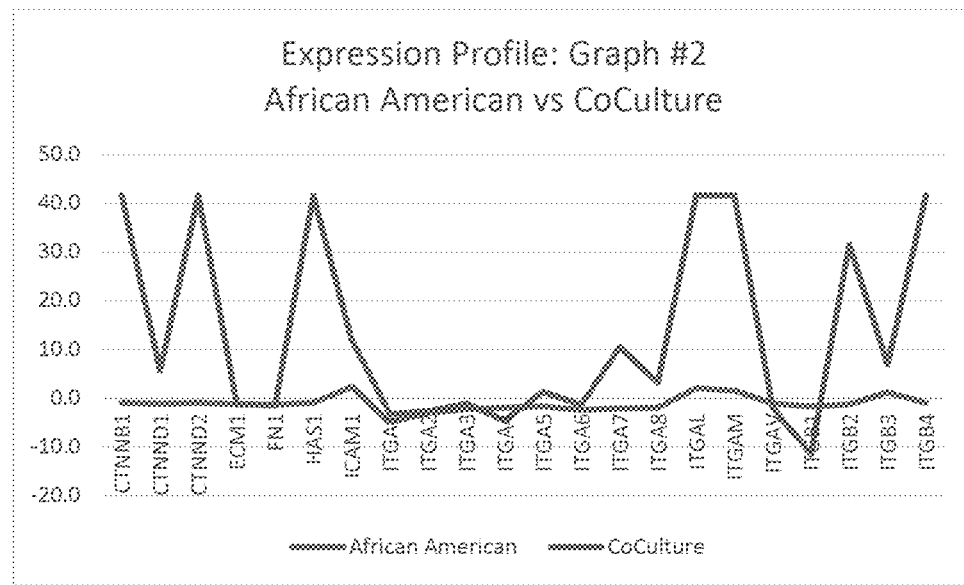
Figure 3:
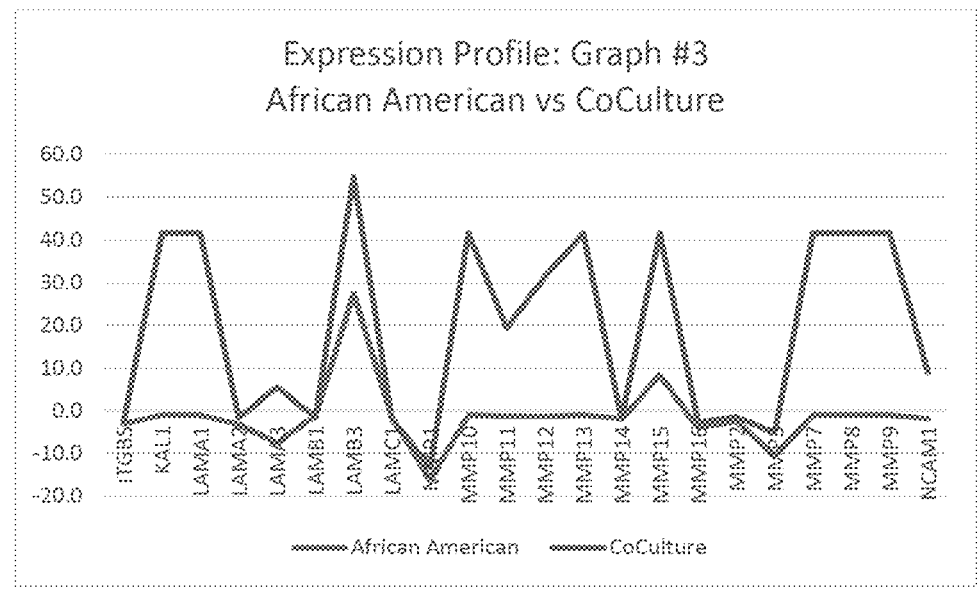
Figure 4:
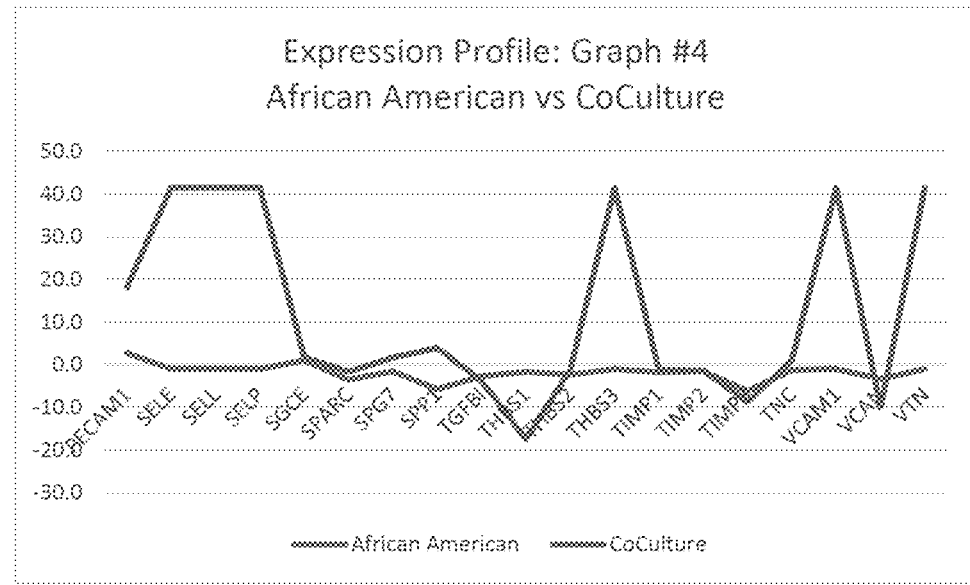

What these tests showed is the ability to mix fibroblasts or cells of different groups or ethnic groups or CoCulturing can be obtained. This can be done at the cell stage, and not just at the cultured media stage. Further, by examining the overall expression profiles (expression values of every gene tested on the array plotted as a line graph), distinct differences in the profiles of African American cells and those African American cells with the Asian/Korean cells, hereinafter called "CoCulture" at a 50:50 ratio were observed. With the Asian/Korean group as control and thus serving as the baseline (or 0 line on the graph), the graphs shown in FIGS. 1-4 clearly demonstrate differences in the overall expression profiles. CoCulture shows a greater magnitude of change than just comparing African American group cells to Asian group cells. In a select few instances, the CoCulture demonstrates a directionally opposed dysregulation from the African American cells (where CoCulture is upregulated, the African American cells are downregulated).

| Functional Gene Group | African American | | CoCulture of African American and Asian/Korean | |
|---|---|---|---|---|
| | % of Group Altered | % of Altered Upregulated | % of Group Altered | % of Altered Upregulated |
| Transmembrane Molecules | 39% | 25% | 77% | 71% |
| Cell-Cell Adhesion | 22% | 50% | 44% | 100% |
| Cell-Matrix Adhesion | 43% | 0% | 76% | 63% |
| Other Adhesion Molecules | 23% | 17% | 65% | 76% |
| Basement Membrane Constituents | 44% | 25% | 44% | 75% |

| Functional Gene Group | African American | | CoCulture of African American and Asian/Korean | |
|---|---|---|---|---|
| | % of Group Altered | % of Altered Upregulated | % of Group Altered | % of Altered Upregulated |
| Collagens & ECM Structural Constituents | 43% | 17% | 43% | 100% |
| ECM Proteases | 28% | 20% | 78% | 71% |
| ECM Protease Inhibitors | 17% | 0% | 50% | 33% |
| Other ECM Molecules | 45% | 0% | 73% | 63% |

The CoCulture exhibits a more stimulatory effect (increased protein production) on the genes of the functional groups, while the African American monoculture demonstrates a more inhibitory (decreased protein production) effect. CoCulture also demonstrates more activity in the genes involved with the majority of the functional groups listed. Only Basement Membrane Constituents and Collagens &ECM Structural Constituent pathways demonstrate the same level of dysregulation (although they still demonstrate a stronger stimulatory effect in the CoCultured cells).

The results of the testing illustrate the following. The enablement for the mixture of fibroblasts cells of two or more donors or different ethnic groups. Further, the test supports distinct differences in the profiles of African American cells than those in CoCulture (50:50 of African American and Asian/Korean). Namely, CoCulture provides: (1) larger stimulatory effect on protein production, (2) a greater degree in pathways related to transmembrane molecules, adhesion molecules (cell-cell; cell-matrix and others), ECM Proteases and inhibitors, (3) different gene expression, (4) significant increase in HAS1 (Hyaluronan Synthase, (5) an increase in COL7A1 (loss of COL7A1 can contribute to wrinkle formation according to scientific literature); and (6) a greater number of MMPs involved.

Accordingly, the tailored and/or customized blending envisioned by the present disclosure even at the cell level clearly has unexpectedly be found can be done.

It should be understood that the present disclosure will be a topical composition. Preferably, the topical composition is a cream applied to the recipient. The cream or cream product will have a vehicle. The vehicle is to allow for the application to the recipient's skin and not obfuscate the effect of the fibroblast mixture. It is believed that a major percentage of the vehicle will be water. It is also envisioned that the amount of the mixture of fibroblast cultures in the total topical composition or cream will be less than 5 percent (%) and preferably less than 1 percent. It is envisioned that less than 1 percent will produce optimum results in a topical composition.

We claim:

1. A topical product tailored for imparting two or more desired skin characteristics to the skin of a recipient, the topical product comprising:
a cream, serum, or lotion having incorporated therein a mixture of at least:
(1) a first culture derived from fibroblasts that have been isolated from a first individual donor having at least one of the two or more desired skin characteristics, and
(2) a second culture derived from fibroblasts that have been isolated from at least a second individual donor having at least the other one of the two or more desired skin characteristics,
wherein the first and second cultures are co-cultured together and modulated,
wherein the modulation increases potency and improves efficacy, and
wherein the modulation is achieved by modifying oxygen levels during the co-culturing of the fibroblasts from the at least first and second donors,
wherein the mixture is formulated to have a greater percentage of the first culture than the second culture based on weighted factors to tailor the topical product to impart the two or more desired skin characteristics to the skin of the recipient,
wherein the first and second individual donors are selected based on their skin characteristics selected from the group consisting of: skin tone, skin elasticity, skin smoothness, reduced scarring, reduced wrinkles, response to inflammatory stimulus, ability to retain moisture, propensity to produce new vasculature, propensity to deliver nutrients, and increase skin thickness or density,
wherein the first and second individual donors are all limited to one gender and each has an ethnic homogeneity that is 80% or greater from a single ethnic race, and
wherein the recipient is not in the single ethnic race so that the topical product is a non-autologous product that imparts the desired two or more skin characteristics on the skin of the recipient when the topical product is applied to the skin of the recipient.

2. The product of claim 1, wherein at least one individual donor of the first and second individual donors is of a second single ethnic race from the plurality of ethnic races.

3. The product of claim 1, wherein the weighted factors are a single factor.

4. The product of claim 1, wherein the weighted factors are a plurality of factors.

5. The product of claim 4, wherein the plurality of factors are of each donor and include an age factor, an ethnic homogeneity factor, a health factor, and a physical beauty factor.

6. The product of claim 5, wherein the beauty factor includes adherence of at least one of the individual donors to a golden ratio.

7. The product of claim 5, wherein the age factor includes donors only between 12 and 35 years of age.

8. The product of claim 5, wherein the age factor includes donors only between 18 and 30 years of age.

9. The product of claim 5, wherein the health factor includes eliminating donors having a genetic disease and premature aging due to environmental conditions.

10. The product of claim 9, wherein the environmental conditions include free radical generation.

11. The product of claim 10, wherein the free radical generation includes sun, smoking and higher neoplasms.

* * * * *